United States Patent [19]

Farge et al.

[11] 4,324,579
[45] Apr. 13, 1982

[54] HERBICIDAL AND PHYTOHORMONAL AMIDOXIMES

[75] Inventors: Daniel Farge, Thiais; Jean Leboul, Gif sur Yvette; Yves Le Goff, Bretigny/Orge; Gilbert Poiget, Thiais, all of France

[73] Assignee: Philargo, Lyons, France

[21] Appl. No.: 116,452

[22] Filed: Jan. 29, 1980

Related U.S. Application Data

[62] Division of Ser. No. 906,863, May 17, 1978, Pat. No. 4,216,006, which is a division of Ser. No. 722,215, Sep. 10, 1976, Pat. No. 4,116,974.

[30] Foreign Application Priority Data

Sep. 11, 1975 [FR] France ............... 75 27884
Jul. 8, 1976 [FR] France ............... 76 21717

[51] Int. Cl.³ .................. A01N 43/36; C07D 207/34
[52] U.S. Cl. ........................................ 71/74; 71/70; 71/72; 71/73; 71/75; 71/77; 71/95; 71/98; 71/103; 71/111; 71/114; 260/326.2; 260/326.22; 260/326.47; 260/349; 560/13; 560/22; 560/29; 560/35; 562/430; 562/437; 562/440
[58] Field of Search ........... 260/326.2, 326.47, 326.22; 71/95, 74, 77

[56] References Cited

U.S. PATENT DOCUMENTS 3,742,056 6/1973 Henderson .................. 548/262
4,260,410 4/1981 Schinski et al. ............... 71/95

FOREIGN PATENT DOCUMENTS 2808317 9/1978 Fed. Rep. of Germany ...... 564/165

Primary Examiner—Alton D. Rollins
Attorney, Agent, or Firm—Robert E. Burns; Emmanuel J. Lobato; Bruce L. Adams

[57] ABSTRACT

Amidoximes of the formula

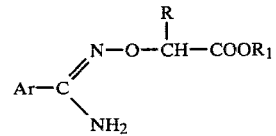

are disclosed. R represents a hydrogen atom on a lower alkyl ($C_1$–$C_4$) or phenyl; $R_1$ represents lower alkyl or a metal atom and Ar represents substituted or unsubstituted phenyl or a five-membered substituted or unsubstituted aromatic heterocyclic group where the hetero atom is selected from the group O, S and N. The compounds have phytohormonal activity at low dosages in plants and herbicidal activity at higher levels.

7 Claims, No Drawings

HERBICIDAL AND PHYTOHORMONAL AMIDOXIMES

This is a division of application Ser. No. 906,863, filed May 17, 1978, now U.S. Pat. No. 4,216,006, which is a division of application Ser. No. 722,215, filed September 10, 1976, now U.S. Pat. No. 4,116,974.

The present invention relates to new derivatives of amidoximes of the general formula:

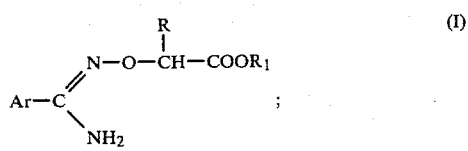

their preparation, the compositions in which they are present, and the treatments carried out with these compositions.

In the general formula (I), R represents a hydrogen atom or an alkyl group containing 1 to 4 carbon atoms, or a phenyl group, $R_1$ represents a hydrogen atom or an alkyl group containing 1 to 4 carbon atoms, or a metal atom, and Ar represents a phenyl group substituted by 1 to 3 substituents which may be identical or different and are chosen from among halogen atoms and the following groups: alkyl containing 1 to 4 carbon atoms, hydroxyl, alkoxy of which the alkyl part contains 1 to 4 carbon atoms, alkylthio of which the alkyl part contains 1 to 4 carbon atoms, alkylsulphinyl of which the alkyl part contains 1 to 4 carbon atoms, alkylsulphonyl of which the alkyl part contains 1 to 4 carbon atoms, trifluoromethyl, trifluoromethoxy, trifluoromethylthio, carboxyl, alkoxycarbonyl of which the alkyl part contains 1 to 4 carbon atoms, nitro, amino, alkylamino of which the alkyl part contains 1 to 4 carbon atoms, dialkylamino of which each alkyl part contains 1 to 4 carbon atoms, acylamino of which the acyl part contains 1 to 4 carbon atoms, alkoxycarbonylamino of which the alkyl part contains 1 to 4 carbon atoms, azido, alkanoyl containing 1 to 4 carbon atoms, sulphamoyl optionally substituted at the nitrogen by one or two alkyl groups, in which case each alkyl part contains 1 to 4 carbon atoms, or phenyl, or Ar represents an aromatic heterocyclic group with 5 chain members which contains an atom of oxygen, sulphur or nitrogen as the hetero-atom and is optionally substituted by a halogen atom, an alkyl group containing 1 to 4 carbon atoms, an alkoxy group of which the alkyl part contains 1 to 4 carbon atoms, an alkylthio group of which the alkyl part contains 1 to 4 carbon atoms or a phenylalkyl group of which the alkyl part contains 1 to 4 carbon atoms and is itself optionally substituted.

According to the invention, the products of the general formula (I) can be obtained in accordance with one of the following methods:

(1) By the action of a product of the general formula:

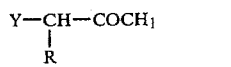

in which R and $R_1$ are defined as above and Y represents a halogen atom, on an amidoxime of the general formula:

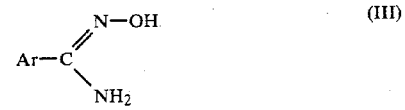

in which Ar is defined as above.

The reaction is generally carried out in an aqueous-organic solvent such as a mixture of ethanol and water or dimethylformamide and water, in the presence of an alkaline condensation agent such as sodium hydroxide, potassium hydroxide or a tetraalkylammonium hydroxide, and at a temperature of between 20° and 80° C.

The products of the general formula (III) can be obtained by the action of hydroxylamine on a nitrile of the general formula:

in which Ar is defined as above.

The reaction is generally carried out in an organic solvent such as aqueous ethanol, at a temperature of between 20° and 80° C.

(2) By the action of a product of the general formula:

in which R and $R_1$ are defined as above, on an imino-ether salt of the general formula:

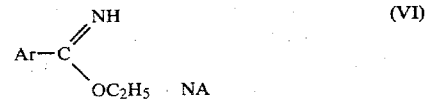

in which Ar is defined as above and HA represents a molecule of hydrochloric acid (HCl) or of fluoboric acid ($HBF_4$).

The reaction is generally carried out in a basic organic solvent such as pyridine, at a temperature of about 20° C.

The salt of an imino-ether, of the general formula (VI), can be obtained either by the action of a solution of hydrogen chloride in ethanol on a nitrile of the general formula (IV), or by the action of triethyloxonium fluoborate (Meerwein salt) on a amide of the general formula:

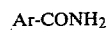

in which Ar is defined as above.

(3) By the action of a compound of the formula:

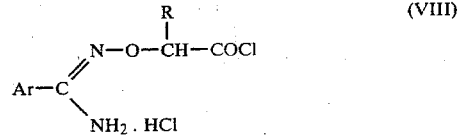

on a compound of the formula $R_1OH$ (IX), where Ar, R and $R_1$ have the same definition as in the formula (I).

The reaction is carried out by heating the compound VIII at a temperature of the order of 60° C. in the presence of the alcohol (IX) and then evaporating the alcohol under reduced pressure.

The products of the general formula (I), in which $R_1$ represents a hydrogen atom, can be obtained by saponification of a product of the general formula (I), in which $R_1$ represents an alkyl group containing 1 to 4 carbon atoms.

The reaction is generally carried out in an organic solvent such as methanol or ethanol in the presence of a base such as sodium hydroxide or potassium hydroxide, at a temperature of about 20° C.

The products of the general formula (I) for which Ar represents a phenyl group substituted by one or more alkylsulphinyl groups can be obtained from the compounds of the general formula (I), for which Ar represents a phenyl group substituted by one or more alkylthio groups, by oxidation of the alkylthio group or groups to alkylsulphinyl groups. The oxidation can be carried out at ordinary temperature by dissolving the compound to be oxidized in acetone and adding a 30% strength (weight/volume) hydrogen peroxide solution to the above solution.

The products according to the present invention exhibit remarkable properties which render them particularly useful in the agricultural field.

If they are used at doses of between 1 and 100 g/hl of water, they exhibit particularly valuable phytohormonal properties. In that case, they possess auxinic actions analogous to those of indolylacetic acid or of derivatives of the phenoxyacetic acids. They are essentially useful in assisting the setting of fruit on certain plants (tomatoes), preventing the shedding of leaves or fruit or increasing the formation of roots.

If they are used at doses of between 0.5 and 10 kg/ha, the products according to the invention exhibit herbicidal properties, in particular against dicotyledon plants, both in pre-emergence and in post-emergence.

For use in practice, the compounds according to the invention are rarely employed by themselves, but instead are employed in the form of agricultural compositions which also form the subject of the present application.

The compositions generally comprise, in addition to the active material according to the invention, a carrier and/or a surface-active agent which are compatible with the active material and can be used in agriculture. In these compositions, the content of active product can be between 0.005 and 95% by weight.

The term "carrier" in the sense of the present description denotes an organic or inorganic, natural or synthetic material, with which the active material is associated in order to facilitate its application to the plant, to the seed or to the soil, or its transport, or its handling. The carrier can be solid (clays, natural or synthetic silicates, resins, waxes, solid fertilizers and the like) or fluid (water, alcohols, ketones, petroleum fractions, chlorinated hydrocarbons or liquified gases).

The surface-active agent can be an emulsifier, a dispersing agent or wetting agent and each of these can be ionic or non-ionic. By way of example there may be mentioned the salts of polyacrylic acids and of ligninsulphonic acids, and condensates of ethylene oxide with fatty alcohols, fatty acids or fatty amines.

The compositions according to the invention can be prepared in the form of wettable powders, dusting powders, granule solutions, emulsifiable concentrates, emulsions, suspensions, suspension concentrates and aerosols.

The wettable powders are usually prepared in such a way that they contain from 20 to 95% by weight of active material, and they usually contain, in addition to a solid carrier, from 0 to 5% of wetting agent, from 3 to 10% by weight of a dispersing agent and, where necessary, from 0 to 10% by weight of one or more stabilizers and/or other additives, such as penetrating agents, adhesives or anti-caking agents, dyestuffs and the like.

By way of example, the composition of a wettable powder is given below, the percentages being expressed by weight:

| | |
|---|---|
| Active material (compound of the formula I) | 50% |
| Calcium lignosulphate (deflocculating agent) | 5% |
| Isopropylnaphthalenesulphonate (wetting agent) | 1% |
| Silica anti-caking agent | 5% |
| Kaolin filler | 39% |

The powders for dusting are usually prepared in the form of a dust concentrate having a composition similar to that of a wettable powder, but without dispersing agent, and are diluted, at the use site, with a supplementary amount of a solid carrier so that a composition which usually contains from 0.5 to 10% by weight of active material is obtained.

The emulsifiable concentrates which can be applied by spraying usually contain, in addition to the solvent and, where necessary, a co-solvent, from 10 to 50% by weight/volume of active material, from 2 to 20% by weight/volume of emulsifiers and from 0 to 20% by weight/volume of appropriate additives, such as stabilizers, penetrating agents, corrosion inhibitors, dyestuffs and adhesives.

By way of example, the composition of an emulsifiable concentrate is given below, the amounts being expressed in g/l:

| | |
|---|---|
| Active material (compound of the formula I) | 400 g/l |
| Dodecylbenzenesulphonate | 24 g/l |
| Nonylphenol oxyethylated with 10 molecules of ethyleneoxide | 16 g/l |
| Cyclohexanone | 200 g/l |
| Aromatic solvent | q.s.p. 1 liter. |

The suspension concentrates, which can also be applied by spraying, are prepared so that a stable fluid product which does not sediment is obtained, and they usually contain from 10 to 75% by weight of active material, from 0.5 to 15% by weight of surface-active agents, from 0.1 to 10% by weight of anti-sedimentation agents such as protective colloids and thixotropic agents, from 0 to 10% by weight of appropriate additives, such as anti-foam agents, corrosion inhibitors, stabilizers, penetrating agents and adhesives and, as the carrier, water or an organic liquid in which the active material is substantially insoluble; certain organic solid materials or inorganic salts can be dissolved in the carrier to assist in preventing the sedimentation or to act as antifreeze agents for the water.

Aqueous dispersions and emulsions, for example compositions obtained by diluting a wettable powder or an emulsifiable concentrate according to the invention with water, also fall within the general scope of the present invention. These emulsions can be of the waterin-oil type or of the oil-in-water type and can have a thick consistency such as that of a "mayonnaise".

For a so-called "ultra-low volume" application, entailing spraying as very fine droplets, solutions, in organic solvents, which contain from 70 to 95% of active material are prepared.

The compositions according to the invention can contain other ingredients, for example protective colloids, adhesives or thickeners, thixotropic agents, stabilizers or sequestering agents as well as other known active materials having pesticidal properties, in particular insecticides or fungicides.

The examples which follow are given, without implying a limitation, in order to illustrate the invention.

EXAMPLE 1

Preparation of O-ethoxycarbonyl-methyl-thiophene-2-carboxyamidoxime

The process used is the second of the processes mentioned in the present application. A mixture of ethyl thiophene-2-carboximidate hydrochloride (140 g.) and ethyl amino-oxyacetate hydrochloride (104 g.) in pyridine (2,350 cc.) is stirred at a temperature of about 20° C. for one hour. The pyridine is evaporated under reduced pressure (2 mm Hg) at a temperature of about 30° C., the residue is then taken up in ethyl acetate (one liter), and the pyridine hydrochloride formed is filtered off and washed with ethyl acetate (2×500 cc.). The filtrate is washed with water (a total of 500 cc), decanted, dried over sodium sulphate and decolorized with animal charcoal. After filtration, and evaporation of the solvent at 30° C. under reduced pressure (20 mm Hg), a limpid oil is obtained, which crystallizes when triturated in isopropyl ether (100 cc.). After isolation by filtration, and drying O-ethoxycarbonyl-methyl-thiophene-2-carboxamidoxime (150.7 g.), melting at 58° C., is obtained. After recrystallization from isopropyl ether (3.3 parts), the pure product, which is in the form of white crystals, melts at 62° C.

EXAMPLES 2 TO 45

On following the same process as in Example 1, with suitable starting materials, the following products of Table I are obtained.

TABLE I $$\text{Ar}-\underset{\underset{NH_2}{\diagdown}}{\overset{\overset{R}{\diagup N-O-CH-COOR_1}}{C}}$$

| Ex. No. | Ar | R | $R_1$ | Yield | Melting point (°C.) after recrystallization | Other characteristics |
|---|---|---|---|---|---|---|
| 2 | —C$_6$H$_4$—OH | H | C$_2$H$_5$ | 73% | 131 | |
| 3 | —C$_6$H$_4$—Cl | H | C$_2$H$_5$ | 100% | 59 | |
| 4 | 5-CH$_3$-thiophen-2-yl | H | C$_2$H$_5$ | 91% | 112 | |
| 5 | 1-CH$_3$-pyrrol-2-yl | H | C$_2$H$_5$ | 75% | 70 | |
| 6 | 3-CH$_3$-thiophen-2-yl | H | C$_2$H$_5$ | 92% | 130 | |
| 7 | —C$_6$H$_4$—OCH$_3$ | H | C$_2$H$_5$ | 59% | 67–68 | |
| 8 | 5-CH$_3$-thiophen-3-yl | H | C$_2$H$_5$ | 92% | 49 | |
| 9 | 5-Br-thiophen-3-yl | H | C$_2$H$_5$ | 73% | 39.5 | |
| 10 | —C$_6$H$_4$—N(CH$_3$)$_2$ | H | C$_2$H$_5$ | 84% | 97 | |
| 11 | 2-Cl-6-NO$_2$-C$_6$H$_3$— | H | C$_2$H$_5$ | 109% | 109 | |
| 12 | 2-Cl-C$_6$H$_4$— | H | C$_2$H$_5$ | 100% | 53 | |
| 13 | 2-SCH$_3$-C$_6$H$_4$— | E | C$_2$H$_5$ | 89% | 75 | |

TABLE I-continued $$\underset{Ar}{\overset{R}{\underset{NH_2}{\overset{N-O-CH-COOR_1}{\diagup}}}}C$$

| # | Ar | R | R₁ | Yield | MP (°C) | Notes |
|---|---|---|---|---|---|---|
| 14 | 3-CF₃-C₆H₄ | H | C₂H₅ | 96% | 87 | |
| 15 | 2-I-C₆H₄ | H | C₂H₅ | 94% | | Boils at 175° C./0.2 mm Hg. |
| 16 | 3-NO₂-C₆H₄ | H | C₂H₅ | 97% | 95 | |
| 17 | 3-OH-C₆H₄ | H | C₂H₅ | 75% | 90 | |
| 18 | 3-F-C₆H₄ | H | C₂H₅ | 100% | 66 | |
| 19 | 2-F-C₆H₄ | H | C₂H₅ | 100% | | Boils at 154° C./0.5 mm Hg. |
| 20 | 3,5-diiodo-4-OH-C₆H₂ | H | C₂H₅ | 97% | 163 | |
| 21 | 5-SCH₃-thien-2-yl | H | C₂H₅ | 93% | 91 | |
| 22 | 2,4-(OCH₃)₂-C₆H₃ | H | C₂H₅ | 87% | 74 | |
| 23 | 3-OH-4-OCH₃-C₆H₃ | H | C₂H₅ | 80% | 100 | |
| 24 | 2-CH₃-C₆H₄ | H | C₂H₅ | 99% | | Boils at 142–148° C./0.4 mm Hg |
| 25 | 5-OCH₃-thien-2-yl | H | C₂H₅ | 95% | 80 | |
| 26 | 4-COOC₂H₅-C₆H₄ | H | C₂H₅ | 92% | 82 | |
| 27 | 4-NHCOC₂H₅-C₆H₄ | H | C₂H₅ | 71% | 141 | |
| 28 | 4-COOH-C₆H₄ | H | C₂H₅ | 98% | 146 | |
| 29 | 5-I-thien-2-yl | H | C₂H₅ | 91% | 124 | |
| 30 | 1-CH₂C₆H₅-pyrrol-2-yl | H | C₂H₅ | 63% | | Chromatographed oil $n_D^{25} = 1.5655$ |
| 31 | 3-SO₂N(CH₃)₂-C₆H₄ | N | C₂H₅ | 91% | 98 | |
| 32 | 3-SO₂NH₂-C₆H₄ | N | C₂H₅ | 84% | 112 | |

TABLE I-continued $$\underset{Ar-C}{\overset{R}{\underset{NH_2}{\diagdown}}}\!\!\!\!\!\overset{N-O-CH-COOR_1}{\diagup}$$

| | AR— | R | R₁ | Yield | Melting point (°C.) or characteristics |
|---|---|---|---|---|---|
| 33 | 2-SCF₃-phenyl | H | C₂H₅ | 98% | 65 |
| 34 | 2-SO₂CH₃-phenyl | H | C₂H₅ | 88% | 118 |
| 35 | 4-NH₂-phenyl | H | C₂H₅ | 82% | — Oil converted to the oxalate boils at 149° C. |
| 36 | 2-Br-phenyl | H | C₂H₅ | 94% | — Boils at 10°/ 0.2 mm Hg |
| 37 | 4-SO₂N(CH₃)₂-phenyl | H | C₂H₅ | 98% | 114 |
| 38 | furyl | H | Na | | 186 |
| 39 | furyl | H | Na | | 214 |

| Examples | AR— | —R | —R₁ | Yield | Melting point (°C.) or characteristics |
|---|---|---|---|---|---|
| 40 | 2-Cl-phenyl | —H | —C₂H₅ | 49% | Boils at 178° C./ 0.4 mm Hg oil |
| 41 | thienyl (S) | —H | —C₂H₅ | 75% | 56° C. |
| 42 | thienyl (S) | —CH₃ | —C₂H₅ | 98% | Oil |
| 43 | Cl-thienyl | —H | —C₂H₅ | 99% | 110° C. |
| 44 | furyl (O) | —H | —C₂H₅ | 65% | 60° C. (Hemihydrate) |
| 45 | pyrrolyl (NH) | —H | —C₂H₅ | 66% | 121° (C.) |

EXAMPLE 46

Preparation of the sodium salt of O-carboxymethyl-thiophene-2-carboxamidoxime.

The process used for this example is the first of the processes described in the present application.

A suspension obtained from bromoacetic acid (29.4 g.) and 0.99 N ethanolic sodium hydroxide solution (213 cc.) is added over the course of 5 minutes to a mixture of thiophene-2-carboxamidoxime (30 g.) and an 0.99 N ethanolic sodium hydroxide solution (213 cc.), and the batch is stirred for 16 hours. The ethanol is evaporated under reduced pressure (20 mm Hg) at a temperature of between 20° C. and 30° C. The crystals obtained are taken up in ethyl acetate (210 cc.), filtered off, washed with ether (2×100 cc.) and dried at a temperature of about 20° C. under reduced pressure (20 mm Hg). The white crystals thus obtained are dissolved in water (390 cc.) and sodium chloride (40 g.) is added, followed, after solution is complete, by the addition of citric acid (15 g.). The precipitate which forms is filtered off and washed and dried. O-Carboxymethyltniophene-2-carboxamidoxime (15.65 g.) melting at 130° C. is thus obtained. On again saturating the mother liquors with sodium chloride and following the above procedure, a second crop of O-carboxymethylthiophene-2-carboxamidoxime, also melting at 130° C., is obtained. After recrystallization from water, the pure product melts at 131° C.

EXAMPLE 47

A mixture of α-bromobutyric acid (16.7 g.) and an 0.97 N ethanolic NaOH solution (103 cc.) is added to the suspension obtained from thiophene-2-carboxamidoxime (14.2 g.) and an 0.97 N ethanolic sodium hydroxide solution (103 cc.). Following the method described in Example 48, the sodium salt of O-(1-carboxypropyl)-thiophene-2-carboxamidoxime (14.1 g.), melting at 246° C., is obtained.

EXAMPLE 48

Preparation of the compounds according to the formula I, with $R_1$=H, by saponification of the compounds for which $R_1$=an alkyl group.

An 0.1 N sodium hydroxide solution (1,250 cc.) is added to a solution of O-ethoxycarbonylmethyl-thiophene-2-carboxamidoxime (22.8 g.) in ethanol (220 cc.). The suspension thus formed is stirred for 40 hours at a temperature of about 20° C. The solution obtained is clarified by filtration over Supercel and neutralized by adding a normal hydrochloric acid solution (125 cc.). The mixture is concentrated to ⅔ of its volume under reduced pressure at a temperature of about 50° C. and is then extracted with methylene chloride (a total of 1,100 cc.). The organic extracts are dried over calcined magnesium sulphate and decolorized by means of decolorizing charcoal. After filtration, and evaporation of the solvent under reduced pressure (20 mm Hg), O-carboxymethyl)-thiophene-2-carboxamidoxine (7 g.) melting at 120° C. is obtained. A second extraction of the mother liquors with ethyl acetate (a total of 750 cc.), followed by a treatment as above, gives a further amount of product (9.1 g.) melting at 129° C.

After recrystallization from water, O-carboxymethylthiophene-2-carboxamidoxime melts at 131° C. This compound has already been described in Example 46 of the present application, where it is obtained in accordance with a different process.

EXAMPLE 49

Preparation of O-butoxycarbonylmethyl-thiophene-2-carboxamidoxime.

The process used for this example is the third of the processes described in the present application.

A mixture of O-chloroformylmethyl-thiophene-2-carboxamidoxime hydrochloric (13 g.) and n-butanol (65 cc.) is heated at 60° C. for 4 hours. The alcohol is evaporated at a temperature of about 40° C. under reduced pressure (20 mm Hg) the residue is then taken up in a solution of sodium bicarbonate (7.7 g.) in water (130 cc.), and the organic substance is extracted with ethyl acetate (3×130 cc.). The organic extracts are washed with water (2×50 cc.) and dried over sodium sulphate. After filtering, and evaporating the solvent under reduced pressure (20 mm Hg) at a temperature of about 40° C., O-butoxycarbonylmethylthiophene-2-carboxamidoxime (13 g.) is obtained in the form of an oil. After dissolution in cyclohexane (100 cc.), the product crystallizes. It is filtered off and dried at a temperature of about 25° C. under reduced pressure (1 mm Hg). O-Butoxycarbonylmethyl-thiophene-2-carboxamidoxime (12.3 g.) melting at 31° C. is thus obtained.

EXAMPLE 50

Following the procedure of the preceding example and starting from O-chloroformylmethyl-thiophene-2-carboxamidoxime hydrochloride (15. g.) and methanol (100 cc), O-methoxycarbonylmethyl-thiophene-2-carboxamidoxime (10.7 g.) melting at 82° C., is obtained.

EXAMPLE 51

This example describes the preparation of O-ethoxycarbonylmethyl-3-methylsulphinyl-benzamidoxime, from the compound described in Example 13, by oxidation of the methylthio substituent, attached to the phenyl group, to give a methylsulphinyl substituent.

A 30% strength (weight/volume) solution of hydrogen peroxide (2.1 cc.) is added to a solution of O-ethoxycarbonylmethyl-3-methylthio-benzamidoxime (5.03 g.) in acetone (100 cc.), and the mixture is left to stand for 7 days. The solvents are evaporated at a temperature of about 30° C. under reduced pressure (20 mm Hg) and the residue is then taken up with methylene chloride (50 cc.) and water (20 cc.). The organic phase is decanted and dried over sodium sulphate. After filtration, and evaporation of the solvent, an oil (5 g.) is obtained, which is chromatographed on a column containing silica (50 g.). Elution with methylene chloride gives unreacted O-ethoxycarbonylmethyl-3-methylthio-benzamidoxime (0.9 g.), followed by O-ethoxycarbonylmethyl-3-methylsulphinylbenzamidoxime (3.5 g.) melting at 58° C. After recrystallization from a mixture of isopropyl ether (25 cc.) and ethanol (5 cc.), the pure product melts at 90° C.

EXAMPLE 52

A condensation product (10 parts) of ethylene oxide and octylphenol in the ratio of 10 molecules of ethylene oxide per molecule of octylphenol is added to a solution of O-ethoxycarbonylmethyl-thiophene-2-carboxamidoxime (25 parts) in a mixture (65 parts) of equal parts of toluene and acetophenone. The solution is used, after dilution with water, at the rate of 100 cc. of this solution per 100 liters of water.

The phytohormonal activity of the products of the present application can be demonstrated in the following tests:

(1) Setting of fruit of tomatoes 1 drop (0.05 cc.) of the solution or suspension of the product to be studied is deposited on the ovary of emasculated flowers of tomato plants. After a period of observation of 5 days, the percentage of fruit formed relative to the comparison is noted.

Used in this way, at a concentration of 10 mg/liter, the product of Example 1 shows a degree of setting of fruit of 100%, relative to the comparison (0%). The fruit formed is devoid of pips.

(2) Propagation of tomato leaves

The 3rd and 4th leaves are taken from tomato stems (Marmande variety) having 5 to 6 leaves. The petiole of each leaf is dipped, over a length of 2 to 3 cm, into the solution to be studied, contained in a test tube. 8 days after starting the experiment, the number of roots formed on the petioles of the treated leaves is counted and measured.

Used in this way, at a concentration of 1 mg/liter, the product of Example 1 causes the formation of 100% of rooted leaves, while the formation is zero in the case of the petioles of the comparison plants.

(3) Shedding of leaves

The experiment is carried out on Coleus. Cuttings formed by a fragment of stem carrying two petioles are dipped in the solution of the product to be studied. The separation of the petiole from the stem is followed as a function of time.

With the comparison plants, the separation is complete after two days.

With the product of Example 3, used at a concentration of 100 mg/liter, no separation whatsoever is observed after one week after starting the experiment.

The herbicidal activity of the products of the general formula (I) can be demonstrated in the following manner:

Seeds of various species, namely wheat (Triticum sativum), lentil (Lens culinaris), radishes (Raphanus sativus), sugar beet (Beta vulgaris) and slender foxtail (Alopecurus agrestis) are sown in plastic pots (160 cc. capacity), containing, to a height of 6 cm, a mixture composed of ⅓ of clean earth, ⅓ of vegetable mould and ⅓ of river sand, at the rate of about 30 seeds per pot. For each concentration of product, two pots of wheat and four pots of the other species are used.

For the purpose of a post-emergence treatment, the sowing is carried out in a greenhouse one week before the start of the experiment, so that the small plants are at the following stage at the time of treatment:

| wheat and foxtail | 3 leaves |
| lentil | 3 leaves |
| beat and radish | 2 well-developed cotyledon leaves. |

The treatment is carried out by spraying the solution or suspension of the product, the pots being placed on a pot-turner. Each pot is given 1 cc. of the solution. The doses of the product to be studied are 1 and 8 kg/ha.

During pre-emergence testing, the seeded surface of the pots is allowed to dry whereupon it is covered by about 1 cm with the same earth mixture. The pots are watered by spraying twice a day. During post emergence testing the treated seedlings are allowed to dry. The earth mixture is then moistened by placing the base of the pots in a dish containing water.

Three weeks after the start of the treatment, the number of plants in each pot is counted, and their height is measured.

The results are expressed in percentages relative to the comparison plants.

The results are summarized in the table which follows:

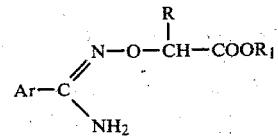

in which
R represents a hydrogen atom or an alkyl group containing 1 to 4 carbon atoms, or a phenyl group,
$R_1$ represents a hydrogen atom or an alkyl group containing 1 to 4 carbon atoms, or a metal atom, and
Ar represents a 5 membered aromatic heterocyclic group which contains an atom of nitrogen as the hetero-atom and is optionally substituted by a halogen atom, an alkyl group an alkoxy group, an alkylthio group or a phenylalkyl group, wherein the alkyl moiety of each of said groups contains 1 to 4 carbon atoms.

2. The compound according to claim 1, of the formula:

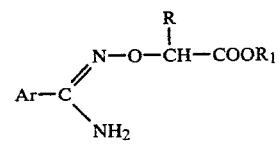

TABLE II

| Product of Example No. | Dose of Product in kg/ha | PRE - EMERGENCE ||||| POST - EMERGENCE |||||
|---|---|---|---|---|---|---|---|---|---|---|---|
| | | Wheat | Lentil | Radish | Beets | Foxtail | Wheat | Lentil | Radish | Beets | Foxtails |
| I | I | 20 | 100 | 75 | 100 | 75 | 0 | 100 | 30 | 50 | 25 |
| I | 10 | 20 | 100 | 100 | 100 | 85 | 20 | 100 | 60 | 70 | 50 |
| 3 | I | 0 | 20 | 0 | 60 | 50 | 0 | 0 | 10 | 30 | 0 |
| 3 | 8 | 0 | 100 | 40 | 90 | 90 | 0 | 40 | 60 | 80 | 20 |
| 5 | I | 0 | 100 | 75 | 0 | 30 | 0 | 60 | 70 | 50 | 0 |
| 5 | 10 | 0 | 100 | 100 | 100 | 50 | 0 | 100 | 100 | 100 | 0 |
| 7 | I | 0 | 20 | 0 | 50 | 50 | 0 | 0 | 0 | 0 | 0 |
| 7 | 10 | 20 | 60 | 0 | 70 | 50 | 0 | 0 | 0 | 0 | 0 |
| 8 | I | 0 | 30 | 0 | 0 | 0 | 0 | 0 | 0 | 0 | 0 |
| 8 | 10 | 0 | 100 | 100 | 100 | 50 | 0 | 100 | 0 | 25 | 0 |
| 9 | I | 0 | 0 | 0 | 0 | 0 | 0 | 0 | 0 | 0 | 0 |
| 9 | 10 | 0 | 25 | 0 | 100 | 75 | 0 | 0 | 0 | 0 | 0 |
| 12 | I | 0 | 0 | 0 | 0 | 0 | 0 | 40 | 60 | 0 | 0 |
| 12 | 10 | 0 | 100 | 0 | 0 | 50 | 0 | 100 | 100 | 50 | 0 |
| 38 | I | 20 | 100 | 0 | 0 | 70 | 0 | 60 | 0 | 50 | 0 |
| 38 | 10 | 70 | 100 | 100 | 100 | 100 | 0 | 100 | 40 | 100 | 20 |
| 39 | I | 10 | 100 | 0 | 50 | 75 | 0 | 50 | 0 | 25 | 50 |
| 39 | 10 | 20 | 100 | 100 | 75 | 80 | 30 | 100 | 25 | 25 | 75 |
| 41 | I | 0 | 100 | 50 | 30 | 75 | 0 | 60 | 60 | 25 | 25 |
| 41 | 10 | 50 | 100 | 100 | 100 | 90 | 0 | 100 | 60 | 50 | 50 |
| 43 | I | 0 | 100 | 0 | 0 | 50 | 0 | 0 | 0 | 0 | 0 |
| 43 | 10 | 30 | 100 | 100 | 100 | 75 | 0 | 60 | 0 | 0 | 0 |
| 44 | I | 0 | 100 | 40 | 0 | 50 | 0 | 75 | 0 | 0 | 0 |
| 44 | 10 | 20 | 100 | 90 | 100 | 80 | 0 | 100 | 80 | 50 | 20 |
| 46 | I | 20 | 100 | 80 | 80 | 75 | 20 | 100 | 40 | 20 | 20 |
| 46 | 10 | 60 | 100 | 100 | 100 | 95 | 20 | 100 | 100 | 100 | 80 |
| 47 | I | 0 | 100 | 0 | 75 | 30 | 0 | 40 | 0 | 0 | 40 |
| 47 | 10 | 0 | 100 | 60 | 100 | 75 | 0 | 40 | 20 | 50 | 40 |

What is claimed:
1. A new amidoxime of the formula in which
R represents a hydrogen atom or an alkyl group of 1–4 carbon atoms,
$R_1$ represents a hydrogen atom, an alkyl group of 1–4 carbon atoms or a metal atom, and
Ar represents a five membered aromatic heterocyclic group which contains a nitrogen atom as the hetero-atom and is optionally substituted by a halogen atom, a methyl group, a methoxy group, a methylthio group or a phenylalkyl group.

3. A composition according to one of claims 1 or 2 in which Ar is the pyrrolyl group.

4. A phytohormonal and herbicidal composition for plants containing, as the active material, at least one compound according to claim 1 in phytohormonal or herbicidally effective amount, in association with a carrier and/or a surface-active agent compatible with the said compound and suitable for agricultural use.

5. The composition according to claim 4, wherein the content of said active material is between 0.005 and 95% by weight.

6. A process for the treatment of plants, wherein said composition according to claim 4 is applied to the plants or their environs.

7. The process of treatment according to claim 6, wherein the dose of active material applied per treated hectare is between 0.5 and 10 kg/ha.

* * * * *